US010653689B2

(12) United States Patent
Hoch et al.

(10) Patent No.: US 10,653,689 B2
(45) Date of Patent: May 19, 2020

(54) COMBINATION-BASED TREATMENT METHOD

(71) Applicant: Nektar Therapeutics, San Francisco, CA (US)

(72) Inventors: Ute Hoch, San Francisco, CA (US); Nancy Marie Burns, Minneapolis, MN (US); Deborah H. Charych, Albany, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 15/111,065

(22) PCT Filed: Jan. 13, 2015

(86) PCT No.: PCT/US2015/011239
§ 371 (c)(1),
(2) Date: Jul. 12, 2016

(87) PCT Pub. No.: WO2015/108876
PCT Pub. Date: Jul. 23, 2015

(65) Prior Publication Data
US 2016/0339013 A1    Nov. 24, 2016

Related U.S. Application Data

(60) Provisional application No. 61/927,376, filed on Jan. 14, 2014, provisional application No. 62/080,775, filed on Nov. 17, 2014.

(51) Int. Cl.
*A61K 31/4745* (2006.01)
*A61K 31/55* (2006.01)
*A61K 45/06* (2006.01)
*A61K 47/60* (2017.01)
*A61K 31/5025* (2006.01)

(52) U.S. Cl.
CPC ...... *A61K 31/4745* (2013.01); *A61K 31/5025* (2013.01); *A61K 31/55* (2013.01); *A61K 45/06* (2013.01); *A61K 47/60* (2017.08)

(58) Field of Classification Search
CPC ............. A61K 31/4745; A61K 47/60; A61K 31/5025; A61K 31/55
USPC .................................................. 514/212.06
See application file for complete search history.

(56) References Cited

U.S. PATENT DOCUMENTS 7,744,861 B2 *   6/2010   Zhao ................ A61K 47/48176
424/426

FOREIGN PATENT DOCUMENTS

| JP | 2006-124351 | | 5/2006 |
|---|---|---|---|
| WO | WO2006033006 A2 | * | 3/2006 |
| WO | WO 2007/084532 A2 | | 7/2007 |
| WO | WO 2007/092646 A2 | | 8/2007 |
| WO | WO 2008/147418 A1 | | 12/2008 |
| WO | WO2008147418 | * | 12/2008 |
| WO | WO 2009/064738 A2 | | 5/2009 |
| WO | WO 2009/073869 A1 | | 6/2009 |
| WO | WO 2011/063156 A2 | | 5/2011 |
| WO | WO 2013/188586 A1 | | 12/2013 |

OTHER PUBLICATIONS

Vogelstein et al. (Nature Medicine (2004), vol. 10, pp. 789-799).*
Kumar et al. (Cancer Res (Sep. 1, 2011), vol. 17, pp. 5626-5634).*
ClinicalTrials.gov [online] (NCT00664781, first received on Apr. 22, 2008), Retrieved from the internet [Retrieved on Feb. 22, 2017] <url: https://clinicaltrials.gov/ct2/show/NCT00664781.*
Gavhane et al. (IJPSR (2011), vol. 2, p. 1-12).*
ClinicalTrials.gov [online] (NCT01012817; first received Nov. 11, 2009) Retrieved from the internet [Retrieved on Feb. 22, 2017] <url: https://clinicaltrials.gov/ct2/show/NCT01012817>.*
Burgess et al. (Frontier in Oncology (2014) vol. 4, pp. 1-15). (Year: 2014).*
Rucaparib PUB CHem CID 993154 [online] Retrieved from the internet, [Retrieved on: Mar. 1, 2018] <url:https://pubchem.ncbi.nlm.nih.gov/compound/rucaparib#section=Top> Document was creasted on Oct. 2006 (Year: 2006).*
Coderoni et al., "Phosphorylation Sites for Type N II Protein Kinase in DNA-Topoisomerase I from Calf Thymus", Int. J. Biochem., vol. 22, No. 7, pp. 737-746, (1990).
Kaiserman et al., "Regulation of *Xenopus laevis* DNA Topoisomerase I Activity by Phosphorylation in Vitro", Biochemistry, vol. 27, pp. 3216-3222, (1988).
Kehrer et al., "Factors Involved in Prolongation of the Terminal Disposition Phase of SN-38: Clinical and Experimental Studies", Clinical Cancer Research, vol. 6, pp. 3451-3458, (Sep. 2000).
Kummar et al., "Advances in using PARP inhibitors to treat cancer", BMC Medicine, vol. 10, No. 25, pp. 1-5, (2012).
Kummar et al., "Phase I Study of PARP Inhibitor ABT-888 in Combination with Topotecan in Adults with Refractory Solid Tumors and Lymphomas", Cancer Res., vol. 71, No. 17, pp. 5626-5634, (2011).
Jameson et al., "A Multicenter, Phase I, Dose-Escalation Study to Assess the Safety, Tolerability, and Pharmacokinetics of Etirinotecan Pegol in Patients with Refractory Solid Tumors", Clin. Cancer Res., vol. 19, No. 1, pp. 268-278, (2012).
Murai et al., "Stereospecific PARP Trapping by BMN 673 and Comparison with Olaparib and Rucaparib", Mol. Cancer Ther., vol. 13, No. 2, pp. 433-443, (2013).
Nektar, "Nektar Presents Preclinical Study Findings for Etirinotecan Pegol (NKTR-102) in Combination with a PARP Inhibitor in BRCA1-deficient Cancer Model", San Francisco, CA, 2 pages, (Nov. 20, 2014).
Patnaik et al., "EZN-2208, a novel anticancer agent, in patient with advanced malignancies: a Phase 1 dose-escalation study", Poster C221, presented at AACR-NCI-EORTC, 2 pages, (2009).

(Continued)

*Primary Examiner* — Taina D Matos Negron
(74) *Attorney, Agent, or Firm* — Susan T. Evans

(57) ABSTRACT

The invention relates to (among other things) a method comprising the steps of (a) administering to a patient a PARP-inhibiting amount of a PARP inhibitor; and (b) administering to the patient a topoisomerase I-inhibiting amount of a long-acting topoisomerase I inhibitor.

11 Claims, 4 Drawing Sheets

(56) References Cited

OTHER PUBLICATIONS

Pommier et al., "Mechanism of action of eukaryotic DNA topoisomerase I and drugs targeted to the enzyme", Biochimica et Biophysica Acta, vol. 1400, pp. 83-106, (1998).
Sabbatino et al., "Effect of p53 Activity on the Sensitivity of Human Glioblastoma Cells to PARP-1 Inhibitor in Combination with Topoisomerase I Inhibitor or Radiation", Cytometry Part A, vol. 85A, pp. 953-961, (2014).
Samuels et al., "DNA Topoisomerase I Phosphorylation in Murine Fibroblasts Treated with 12-O-Tetradecanoylphorbol-13-acetate and in Vitro by Protein Kinase C", The Journal of Biological Chemistry, vol. 267, No. 16, Issue of Jun. 5, pp. 11156-11162, (1992).
Sapra et al., "Marked therapeutic efficacy of a novel poly(ethyleneglycol) conjugated SN38 conjugate in xenograft models of breast and colorectal cancers", Abstract 145.
Shen et al., BMN 673, a Novel and Highly Potent PARP1/2 Inhibitor for the Treatment of Human Cancers with DNA Repair Deficiency:, Clin. Cancer Res., vol. 19, No. 18, pp. 5003-5015, (2013).
Siegel et al., "Cancer Statistics, 2013", CA Cancer J. Clin., vol. 63, pp. 11-30, (2013).
Stewart et al., "Targeting the DNA Repair Pathway in Ewing Sarcoma", Cell Reports, vol. 9, pp. 829-840, (2014).
Tentori et al., "Inhibition of poly(ADP-ribose) polymerase prevents irinotecan-induced intestinal damage and enhances irinotecan/temozolomide efficacy against colon carcinoma", The FASEB Journal, vol. 20, pp. 1709-1711, (Aug. 2006).
Turman et al., "A Casein Kinase Type II (CKII)-like Nuclear Protein Kinase Associates with, Phosphorylates, and Activates Topoisomerase I", Biochemical Medicine and Metabolic Biology, vol. 50, pp. 210-225, (1993).
Wang, "DNA Topoisomerases", Annu. Rev. Biochem., vol. 65, pp. 635-692, (1996).
PCT International Search Report and Written Opinion corresponding to PCT Application No. PCT/US2015/011239 dated Mar. 16, 2015.
PCT International Preliminary Report on Patentability corresponding to PCT Application No. PCT/US2015/011239 dated Jul. 28, 2016.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003—$1^{st}$, (Jan. 2003).
NOF Corporation, PEG Derivatives, Phospholipid and Drug Delivery Materials for Pharmaceuticals, 27 pages, Catalogue 2003—$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Livraghi et al., "PARP inhibitors in the management of breast cancer: current data and future prospects", BMC Medicine, vol. 13, No. 188, pp. 1-16, (2015).
Australian Examination Report No. 1 corresponding to Australian Patent Application No. 2015206667 dated Apr. 23, 2019.
European Summons to attend oral proceedings corresponding to European Patent Application No. 15704116.1 dated Jun. 7, 2019.
English Translation of Japanese Notice of Reasons for Rejection corresponding to Japanese Patent Application No. 2016-563904 dated Jan. 31, 2019.
English Translation of Mexican $1^{st}$ Requirement of the substantive examination report corresponding to Mexican Patent Application No. MX/a/2016/009167 dated May 28, 2019.

* cited by examiner

COMBINATION-BASED TREATMENT METHOD

CROSS REFERENCE TO RELATED APPLICATIONS

This application is a 35 U.S.C. § 371 application of International Application No. PCT/US2015/011239, filed Jan. 13, 2015, designating the United States, which claims the benefit of priority under 35 U.S.C. § 119(e) to U.S. Provisional Patent Application No. 61/927,376 filed Jan. 14, 2014, and to U.S. Provisional Patent Application No. 62/080,775 filed Nov. 17, 2014, the disclosures of which are incorporated by reference in their entireties.

FIELD OF THE INVENTION

This invention relates to (among other things) the field of cancer chemotherapy and involves the treatment of an individual suffering from a cancer by administering to the patient a long acting topoisomerase I inhibitor and a PARP inhibitor.

BACKGROUND OF THE INVENTION

Topoisomerase I is an enzyme that plays important and critical role in cellular proliferation. In particular, topoisomerase I catalyzes the uncoiling of DNA during replication and transcription. See Pommier et al. (1998) *Biochim. Biophys. Acta.* 1400(1-3):83-105 and Wang (1996) *Annu. Rev. Biochem.* 65:635-92). Thus, by inhibiting this enzyme, highly proliferative cells are preferentially targeted and unable to propagate. As a consequence, this enzyme is a highly attractive target for chemotherapeutic agents, especially in human cancers.

The activity of topoisomerase I is regulated by phosphorylation, primarily on serine residues [Turman et al. (1993) *Biochem. Med. Metab. Biol.* 50(2):210-25; Coderoni et al. (1990) *Int. J. Biochem.* 22(7):737-46; Kaiserman et al. (1988) *Biochemistry* 27(9):3216-22; Samuels et al. (1992) *J. Biol. Chem.* 267(16): 1156-62)], and appears to be necessary for the initial complex formation between the enzyme and DNA (Coderoni et al. (1990) *Int. J. Biochem.* 22(7):737-46).

The poly (ADP-ribose) polymerase ("PARP") family of enzymes plays a critical role in the maintenance of DNA integrity by binding to DNA and repairing single strand breaks (known as "nicks"). PARP1 is overexpressed in a variety of cancers, and its expression has been associated with overall prognosis in cancer, especially breast cancer. PARP inhibitors are believed to bind to PARP, thereby inhibiting its DNA-repair activity as well as preventing the release of PARP from DNA. Inhibition of the activity of PARP1, and a related isoform, PARP2 has shown clinical activity in a several cancers. Kunmar et al. (2012) *BMC Medicine* 10(25):1-5.

Although both topoisomerase I inhibitors, PARP inhibitors and other antineoplastic agents have been proposed to treat patients suffering from cancer with varying degrees of success, one in four deaths in the United States is due to cancer. Siegel et al. (2013) *CA Cancer J. Clin.* 63:11-30. Although treatment regimens involving a single antineoplastic agent are often sought, combinations of known antineoplastic agents can be highly effective as well. Thus, there remains a need to provide (among other things) treatment regimens where combination strategies show enhanced efficacy.

The present invention seeks to address these and other needs in the art.

SUMMARY OF THE INVENTION

In one or more embodiments of the invention, a method is provided, the method comprising the steps of (a) administering to a patient a PARP-inhibiting amount of a PARP inhibitor, and (b) administering to the patient a topoisomerase I-inhibiting amount of a long-acting topoisomerase I inhibitor. By way of clarity, with regard to the sequence of steps in accordance with this method, unless otherwise indicated, the method is not limited to the sequence of steps and step (a) can be performed before, after or simultaneously with, performing step (b).

Additional embodiments of the invention are set forth in the following description and claims.

DETAILED DESCRIPTION OF THE INVENTION

Figure 1:
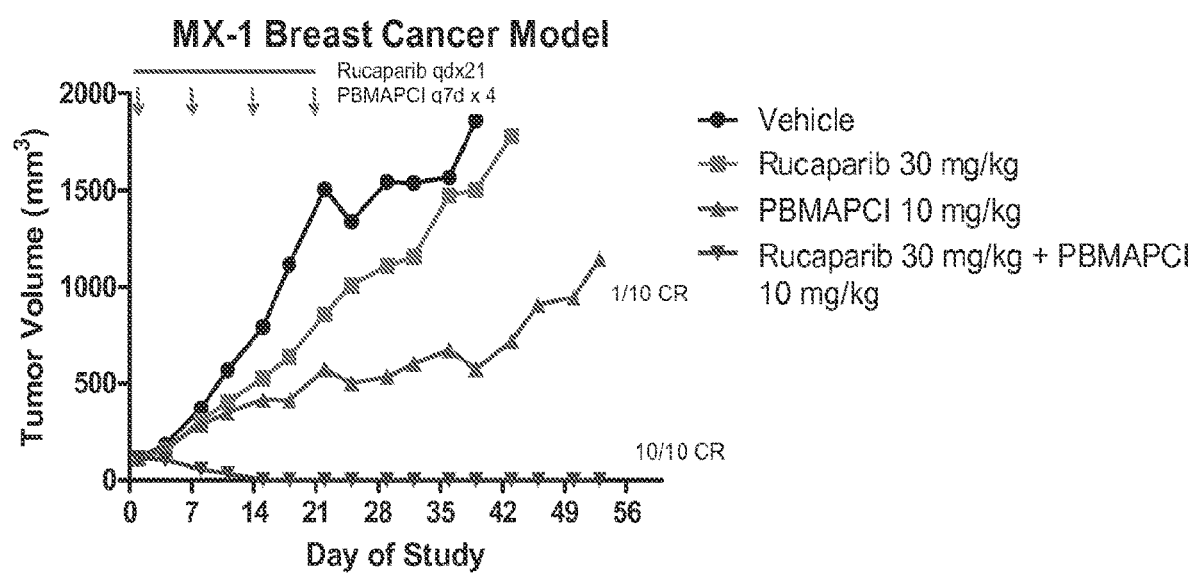
FIG. 1 shows mean tumor volumes in various treatment groups of a MX-1 breast cancer model in mice conducted as described in Example 1.

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic polymer" refers to a polymer that is at least 35% (by weight) soluble, preferably greater than 70% (by weight), and more preferably greater than 95% (by weight) soluble, in water at room temperature. Typically, an unfiltered aqueous preparation of a "water-soluble" polymer transmits at least 75%, more preferably at least 95%, of the amount of light transmitted by the same solution after filtering. It is most preferred, however, that the water-soluble polymer is at least 95% (by weight) soluble in water or completely soluble in water. With respect to being "non-peptidic," a polymer is non-peptidic when it has less than 35% (by weight) of amino acid residues.

The terms "monomer," "monomeric subunit" and "monomeric unit" are used interchangeably herein and refer to one of the basic structural units of a polymer. In the case of a homo-polymer, a single repeating structural unit forms the polymer. In the case of a co-polymer, two or more structural units are repeated—either in a pattern or randomly—to form the polymer. Preferred polymers used in connection with the present invention are homo-polymers. The water-soluble, non-peptidic polymer comprises one or more monomers serially attached to form a chain of monomers.

"PEG" or "polyethylene glycol," as used herein, is meant to encompass any water-soluble poly(ethylene oxide). Unless otherwise indicated, a "PEG polymer" or a polyethylene glycol is one in which substantially all (preferably all) monomeric subunits are ethylene oxide subunits, though, the polymer may contain distinct end capping moieties or functional groups, e.g., for conjugation. PEG polymers for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG polymers, the variable (n) ranges from about 3 to 4000, and the terminal groups and architecture of the overall PEG can vary.

"Branched," in reference to the geometry or overall structure of a polymer, refers to a polymer having two or more polymer "arms" extending from a branch point.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two atoms within a given molecule but also on the substituents attached to these atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Pharmaceutically acceptable excipient" or "pharmaceutically acceptable carrier" refers to a component that may be included in the compositions of the invention causes no significant adverse toxicological effects to a patient.

The term "patient," refers to a living organism suffering from or prone to a condition that can be prevented or treated by administration of a compound of the invention as described herein, and includes both humans and animals. In some instances (such as a method that treats a patient suffering from breast cancer), the patient is preferably a human adult. In still other instances (such as a method that treats a patient suffering from Ewing sarcoma), the patient preferably has an age ranging from 3 to 22, and includes a human child and a human young adult.

As indicated above, the present invention is directed to (among other things) a method comprising the steps of (a) administering to a patient a PARP-inhibiting amount of a PARP inhibitor; and (b) administering to the patient a topoisomerase I-inhibiting amount of a long-acting topoisomerase I inhibitor. With respect to administering steps (a) and (b), these administering steps can be performed in either order (as well as simultaneously) and the invention is not limited in this regard. In one or more embodiments of the invention, administering step (a) will be carried out before administering step (b). In one or more embodiments of the invention, administering step (b) will be carried out before administering step (a). In one or more embodiments, both administering steps (a) and (b) will be carried out simultaneously. Further, in one or more embodiments, steps (a) and/or (b) will be administered repeatedly.

In those instances where administering to a patient a PARP-inhibiting amount of a PARP inhibitor occurs prior to administering to the patient a topoisomerase I-inhibiting amount of a long-acting topoisomerase I inhibitor, the amount of time that passes after administering the PARP inhibitor prior to administering the long acting topoisomerase I inhibitor is preferably within one of the following ranges: from about one minute to about sixty days; from about one minute to about thirty days; from about one minute to about 21 days; from about ten minutes to about 21 days; from about twenty minutes to about 21 days; from about thirty minutes to about 21 days; from about forty minutes to about 21 days; from about sixty minutes to about 21 days; from about two hours to about 21 days; from about four hours to about 21 days; from about six hours to about 21 days; from about eight hours to about 21 days; from about ten hours to about 21 days; from about twelve hours to about 21 days; from about one day to about 21 days; from about two days to about 21 days; from about three days to about 21 days; from about four days to about 21 days; from about five days to about 21 days; from about six days to about 21 days; from about seven days to about 21 days; from about eight days to about 21 days; from about nine days to about 21 days; from about ten days to about 21 days; from about 14 days to about 21 days; from about one minute to about 14 days; from about ten minutes to about 14 days; from about twenty minutes to about 14 days; from about thirty minutes to about 14 days; from about forty minutes to about 14 days; from about sixty minutes to about 14 days; from about two hours to about 14 days; from about four hours to about 14 days; from about six hours to about 14 days; from about eight hours to about 14 days; from about ten hours to about 14 days; from about twelve hours to about 14 days; from about one day to about 14 days; from about two days to about 14 days; from about three days to about 14 days; from about four days to about 14 days; from about five days to about 14 days; from about six days to about 14 days; from about seven days to about 14 days; from about eight days to about 14 days; from about nine days to about 14 days; from about ten days to about 14 days; from about one minute to about 8 days; from about ten minutes to about 8 days; from about twenty minutes to about 8 days; from about thirty minutes to about 8 days; from about forty minutes to about 8 days; from about sixty minutes to about 8 days; from about two hours to about 8 days; from about four hours to about 8 days; from about six hours to about 8 days; from about eight hours to about 8 days; from about ten hours to about 8 days; from about twelve hours to about 8 days; from about one day to about 8 days; from about two days to about 8 days; from about three days to about 8 days; from about four days to about 8 days; from about five days to about 8 days; from about six days to about 8 days; from six days to about 15 days; from about 13 days to about 22 days; from about 20 days to about 22 days; from about 20 days to about 29 days; from about 27 days to about 30 days; from about 27 days to about 45 days; and from about 45 days to about 75 days.

In those instances where administering to a patient a topoisomerase I-inhibiting amount of a long-acting topoisomerase I inhibitor occurs prior to administering to the patient a PARP-inhibiting amount of a PARP inhibitor, the amount of time that passes after administering the long acting topoisomerase I inhibitor prior to administering the PARP inhibitor is preferably within one of the following ranges: from about one minute to about sixty days; from about one minute to about thirty days; from about one minute to about 21 days; from about ten minutes to about 21 days; from about twenty minutes to about 21 days; from about thirty minutes to about 21 days; from about forty minutes to about 21 days; from about sixty minutes to about 21 days; from about two hours to about 21 days; from about four hours to about 21 days; from about six hours to about 21 days; from about eight hours to about 21 days; from about ten hours to about 21 days; from about twelve hours to about 21 days; from about one day to about 21 days; from about two days to about 21 days; from about three days to about 21 days: from about four days to about 21 days; from about five days to about 21 days; from about six days to about 21 days; from about seven days to about 21 days; from about eight days to about 21 days; from about nine days to about 21 days; from about ten days to about 21 days; from about 14 days to about 21 days; from about one minute to about 14 days; from about ten minutes to about 14 days; from about twenty minutes to about 14 days; from about thirty minutes to about 14 days; from about forty minutes to about 14 days; from about sixty minutes to about 14 days; from about two hours to about 14 days; from about four hours to about 14 days; from about six hours to about 14 days; from about eight hours to about 14 days; from about ten hours to about 14 days; from about twelve hours to about 14 days; from about one day to about 14 days; from about two days to about 14 days; from about three days to about 14 days; from about four days to about 14 days; from about five days to about 14 days; from about six days to about 14 days; from about seven days to about 14 days; from about eight days to about 14 days; from about nine days to about 14 days; from about ten days to about 14 days; from about one minute to about 8 days; from about ten minutes to about 8 days; from about twenty minutes to about 8 days; from about thirty minutes to about 8 days; from about forty minutes to about 8 days; from about sixty minutes to about 8 days; from about two hours to about 8 days; from about four hours to about 8 days; from about six hours to about 8 days; from about eight hours to about 8 days; from about ten hours to about 8 days; from about twelve hours to about 8 days; from about one day to about 8 days; from about two days to about 8 days; from about three days to about 8 days; from about four days to about 8 days; from about five days to about 8 days; from about six days to about 8 days; from six days to about 15 days; from about 13 days to about 22 days; from about 20 days to about 22 days; from about 20 days to about 29 days; from about 27 days to about 30 days; from about 27 days to about 45 days; and from about 45 days to about 75 days.

In one or more embodiments of the invention, an initiation phase, a dual phase, and then a maintenance phase is followed. In the initiation phase of a method for treating a patient suffering from cancer, the initiation phase represents the long acting topoisomerase I inhibitor and PARP inhibitor being administered to the patient within 24 hours with each other. Thereafter, in the dual phase of a method for treating a patient suffering from cancer, the dual phase represents administration of the long acting topoisomerase I inhibitor and the PARP inhibitor being administered periodically (e.g., the long acting topoisomerase I inhibitor being administered twice a week to once monthly and the PARP inhibitor being administered daily). The dual phase may continue for one administration, two administrations, three administrations, four administrations, five administrations, six administrations, seven administrations, eight administrations, nine administrations, ten administrations, eleven administrations or twelve administrations of the long acting topoisomerase I inhibitor. Following the dual phase, a maintenance phase occurs where only the PARP inhibitor is administered. Thus, for example, in one or more embodiments of the invention, the steps of (a) administering to a patient a PARP-inhibiting amount of a PARP inhibitor, and of (b) administering to the patient a topoisomerase I-inhibiting amount of a long-acting topoisomerase I inhibitor, are carried out at least twice, followed by a maintenance phase wherein the patient is administered a PARP-inhibiting amount of a PARP inhibitor without any further administration of the long-acting topoisomerase I inhibitor.

The method described herein involves the administration of a long acting topoisomerase I inhibitor. In this regard, the invention is not limited to any specific topoisomerase I inhibitor so long as the topoisomerase I inhibitor is long acting. A topoisomerase I inhibitor is long acting when the effective half-life of the topoisomerase inhibitor satisfies one or more of the following ranges: from about 5 days to about 60 days; from about 9 days to about 60 days; from about 13 days to about 60 days; from about 21 days to about 60 days; from about 28 days to about 60 days; from about 35 days to about 60 days; from about 42 days to about 60; and from about 49 days to about 60 days. With regard to the effective half-life of a drug such as a topoisomerase I inhibitor, some topoisomerase I inhibitors metabolize into SN-38, which can be primarily responsible for the inhibitory activity of topoisomerase I. As such, those topoisomerase I inhibitors that metabolize into SN-38 often describe their half-lives in terms of the elimination of SN-38 (rather than on the elimination of the initially administered topoisomerase I inhibitor). Thus, as used herein, the "effective" half-life of a topoisomerase I inhibitor drug is the half-life of the entity—whether the originally administered drug or a metabolite of the originally administered drug—most responsible for the inhibitory activity of topoisomerase I. By way of example, the literature reports the effective half-life of irinotecan (based on the elimination of SN-38) is about two days, while the effective half-life (again, based on the elimination of SN-38) of a topoisomerase-inhibitor polymer conjugate is about fifty days. See Kehrer et al. (2000) *Clin. Can. Res.* 6:3451-3458 and Gayle S. Jameson et al. (2013) *Clin. Can. Res.* 19:268-278, respectively.

Exemplary and non-limiting examples of long acting topoisomerase I inhibitors include compounds encompassed by the following formula:

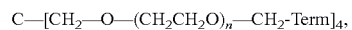

$$C-[CH_2-O-(CH_2CH_2O)_n-CH_2\text{-Term}]_4,$$

wherein: n, in each instance, is an integer having a value from 5 to 150 (e.g., about 113); and Term, in each instance, is selected from the group consisting of —OH, —C(O)OH,

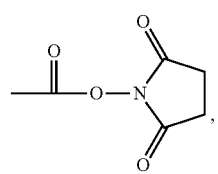

and —NH—CH$_2$—C(O)—O-Irino, wherein Irino is a residue of irinotecan, and, in a composition of such compounds, at least 90% are Irino and the remaining 10% are selected from the group consisting of —OH, —C(O)OH,

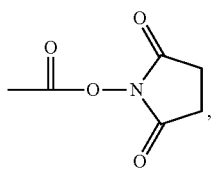

and pharmaceutically acceptable salts (included mixed salts) thereof. These and other compounds and compositions are described in WO 2011/063156.

Additional exemplary and non-limiting examples of long acting topoisomerase I inhibitors include compounds encompassed by the following formula:

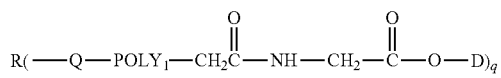

wherein:

R is an organic radical possessing from 3 to 150 carbon atoms,

Q is a linker, wherein R, when taken together with Q to form $R(\sim Q-)_q$, is a residue of a polyol or a polythiol after removal of "q" hydroxyl or thiol protons, respectively to form a point of attachment for $POLY_1$ $POLY_1$ is a water-soluble, non-peptidic polymer selected from the group consisting of poly(alkylene glycol), poly (olefinic alcohol), poly(vinylpyrrolidone), poly(hydroxylalkyl-methacrylamide), poly(hydroxyalkyl-methacrylate), poly($\alpha$-hydroxy acid), poly(acrylic acid), poly(vinyl alcohol), polyphosphazene, polyoxazoline, poly(N-acryloylmorpholine), and copolymers or terpolymers thereof, D is a camptothecin attached at its 10-, 11- or 20-ring position, and q has a value from 3 to 50, and pharmaceutically acceptable salts (included mixed salts) thereof. For example, the following pentaerythritol-based multi-arm structures are exemplary and non-limiting compounds that are long acting topoisomerase I inhibitors:

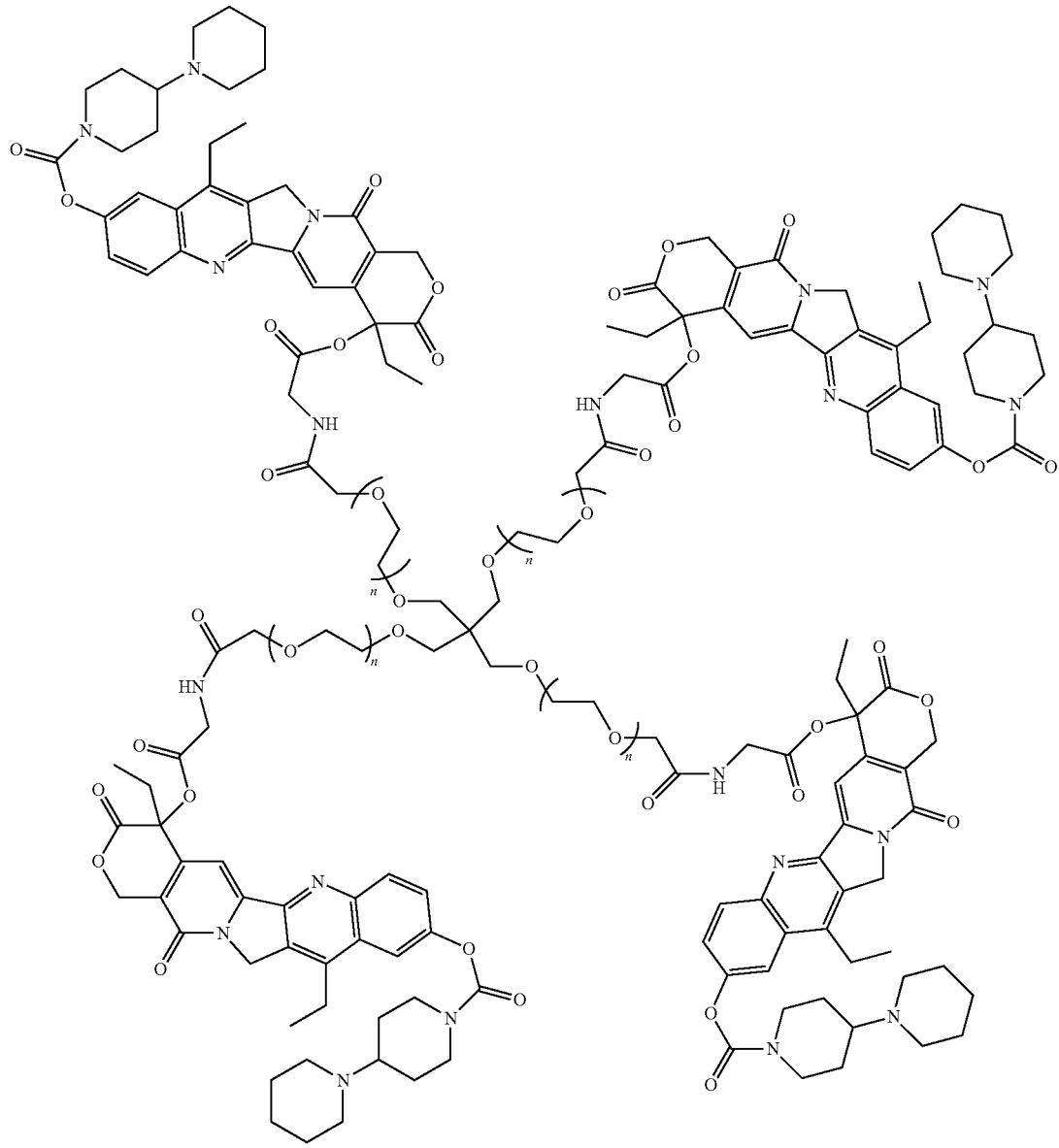

wherein each n is an integer ranging from 40 to about 500 (e.g., about 113 and about 226), and pharmaceutically acceptable salts (included mixed salts) thereof. The above and other compounds are described in U.S. Pat. No. 7,744,861, and are considered "pentaerythritol-based multi-arm polymer conjugates of irinotecan" or a "PBMAPCI."

Further additional exemplary and non-limiting examples of long acting topoisomerase I inhibitors include compounds encompassed by the following formula

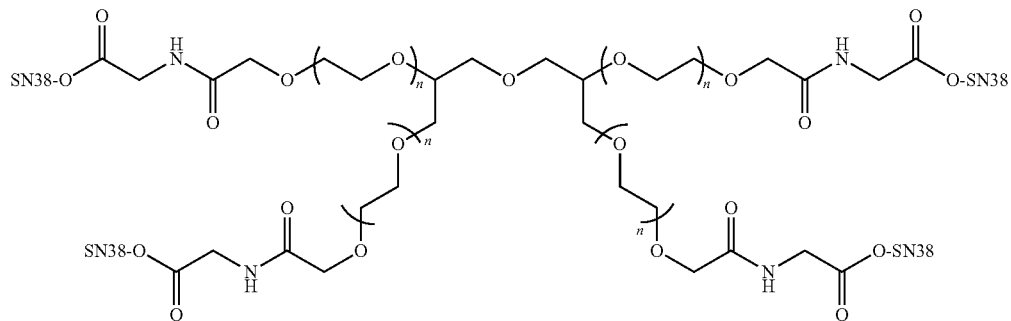

wherein each (n) is a positive integer from about 28 to about 341 and each SN38 is a residue of SN-38. These and other compounds are described in WO 2007/092646, Sapra et al. Abstract 145 entitled "Marked therapeutic efficacy of a novel poly(ethylene-glycol) conjugated SN38 conjugate in xenograft models of breast and colorectal cancers," Patnaik et al. (2009) Poster C221 presented at AACR-NCI-EORTC.

The method described herein involves the administration of a PARP inhibitor. In this regard, the invention is not limited to any specific PARP inhibitor. By way of exemplary PARP inhibitors, the PARP inhibitor can be one selected from the group consisting of rucaparib, olaparib, veliparib, MK-4827, BMN 673, CEP-9722, and E7016.

Assays for determining whether a given compound can act as a PARP inhibitor can be determined through routing experimentation by one of ordinary skill in the art.

In accordance with the method described herein, the PARP inhibitor is administered to a patient in a PARP-inhibiting amount. One of ordinary skill in the art can determine how much a given PARP inhibitor is sufficient to provide clinically relevant inhibition of PARP. For example, one of ordinary skill in the art can refer to the literature and/or administer a series of increasing amounts the PARP inhibitor and determine which amount or amounts provide clinically relevant inhibition of PARP.

In one or more instances, however, the PARP-inhibiting amount is an amount encompassed by one or more of the following ranges: from about 0.01 mg/kg to about 1000 mg/kg; from about 0.1 mg/kg to about 1000 mg/kg; from about 2 mg/kg to about 900 mg/kg; from about 3 mg/kg to about 800 mg/kg; from about 4 mg/kg to about 700 mg/kg; from about 5 mg/kg to about 600 mg/kg; from about 6 mg/kg to about 550 mg/kg; from about 7 mg/kg to about 500 mg/kg; from about 8 mg/kg to about 450 mg/kg; from about 9 mg/kg to about 400 mg/kg; from about 5 mg/kg to about 200 mg/kg; from about 2 mg/kg to about 150 mg/kg; from about 5 mg/kg to about 100 mg/kg; from about 10 mg/kg to about 100 mg/kg; and from about 10 mg/kg to about 60 mg/kg.

In accordance with the method described herein, the long acting topoisomerase I inhibitor is administered to a patient in a topoisomerase I-inhibiting amount. One of ordinary skill in the art can determine how much a given topoisomerase I inhibitor is sufficient to provide clinically relevant inhibition of topoisomerase I. For example, one of ordinary skill in the art can refer to the literature and/or administer a series of increasing amounts the topoisomerase inhibitor and determine which amount or amounts provide clinically relevant inhibition of topoisomerase I.

In one or more instances, however, the topoisomerase I-inhibiting amount (particularly with respect to a pentaerythritol-based multi-arm polymer conjugate of irinotecan) is an amount encompassed by one or more of the following ranges: from about 1 mg/m$^2$ to about 1000 mg/m$^2$ of body surface; from about 2 mg/m$^2$ to about 900 mg/m$^2$ of body surface; from about 3 mg/m$^2$ to about 800 mg/m$^2$ of body surface; from about 4 mg/m$^2$ to about 700 mg/m$^2$ of body surface; from about 5 mg/m$^2$ to about 600 mg/m$^2$ of body surface; from about 6 mg/m$^2$ to about 550 mg/m$^2$ of body surface; from about 7 mg/m$^2$ to about 500 mg/m$^2$ of body surface; from about 8 mg/m$^2$ to about 450 mg/m$^2$ of body surface; from about 9 mg/m$^2$ to about 400 mg/m$^2$ of body surface; from about 10 mg/m$^2$ to about 350 mg/m$^2$ of body surface; from about 20 mg/m$^2$ to about 200 mg/m$^2$ of body surface; from about 30 mg/m$^2$ to about 200 mg/m$^2$ of body surface; from about 40 mg/m$^2$ to about 270 mg/m$^2$ of body surface; and from about 50 mg/m$^2$ to about 240 mg/m$^2$ of body surface.

For confirmation, as used herein with regard to PARP-inhibiting amounts of the PARP inhibitor and topoisomerase I-inhibiting amounts of the long-acting topoisomerase I inhibitor, the amount and extent of the inhibition can vary widely and the combination still be useful in treating patients. For example, an amount of a PARP inhibitor that only minimally inhibits PARP can still be a PARP-inhibiting amount as used herein so long as the method of the claimed invention results in a clinically meaningful response. So too, an amount of a long-acting topoisomerase I inhibitor that only minimally inhibits topoisomerase I for a sufficiently extended period of time can still be a long-acting topoisomerase I inhibitor so long as the method of the claimed invention results in a clinically meaningful response. In some instances, due to (for example) synergistic responses, minimal inhibition of PARP may only be required in the presence of topoisomerase I inhibition. In still other instances, due to (for example) synergistic responses, minimal inhibition of topoisomerase I may only be required in the presence of PARP inhibition. Thus, PARP-inhibiting amounts of the PARP inhibitor and topoisomerase I-inhibiting amounts of the long-acting topoisomerase I inhibitor can range widely in the context of the claimed invention and such amounts are not to be solely based on the amount of a drug as in the monotherapy context necessary to inhibit the given enzyme alone.

The actual dose to be administered will vary depend upon the age, weight, and general condition of the subject as well as the severity of the condition being treated, the judgment of the health care professional, and conjugate being administered.

The unit dosage of any given long acting topoisomerase I and PARP inhibitor can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once clinical benefit is no longer achieved, dosing (whether it is at that point in the therapy a single agent or a combination) is halted.

With respect to the length of time associated with the course of therapy, a typical course of therapy will vary depending on the judgment of the clinician, needs of the patient, and so forth. Exemplary lengths of time associated with the course of therapy in accordance with the claimed method include: about one week; two weeks; about three weeks; about four weeks; about five weeks; about six weeks; about seven weeks; about eight weeks; about nine weeks; about ten weeks; about eleven weeks; about twelve weeks; about thirteen weeks; about fourteen weeks; about fifteen weeks; about sixteen weeks; about seventeen weeks; about eighteen weeks; about nineteen weeks; about twenty weeks; about twenty-one weeks; about twenty-two weeks; about twenty-three weeks; about twenty four weeks; about seven months; about eight months; about nine months; about ten months; about eleven months; about twelve months; about thirteen months; about fourteen months; about fifteen months; about sixteen months; about seventeen months; about eighteen months; about nineteen months; about twenty months; about twenty one months; about twenty-two months; about twenty-three months; about twenty-four months; about thirty months; about three years; about four years and about five years. During this time, it is understood that that one of the long acting topoisomerase I inhibitor or the PARP inhibitor may be administered without the other agent (so long as the both the topoisomerase I inhibitor and the PARP inhibitor are administered as part of a combination therapy as described herein).

The invention provides a method for that is useful for (among other things) treating a patient suffering from a condition that is responsive to treatment with the compound. For example, patients may be responsive to the individual agents alone as well as the combination, but are more responsive to the combination. By way of further example, patients may be non-responsive to one of the individual agents, but are responsive to the combination. By way of still further example, patients may be non-responsive to either of the individual agents alone, but are responsive to the combination.

The method comprises administering a therapeutically effective amount of the given topoisomerase inhibitor. Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

The presently described method wherein a PARP inhibitor and a long-acting topoisomerase I inhibitor are administered to a patient may be used to treat any condition that can be remedied or prevented by this approach. Exemplary conditions are cancers, such as, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewings sarcoma, leiomyosarcoma, rhabdomyosarcoma, colon carcinoma, pancreatic cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, lung cancer, small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma and leukemias.

All articles, books, patents, patent publications and other publications referenced herein are incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

Example 1

Tumor Growth Delay of MX-1 Human Breast Cancer Model with Treatment of PBMAPCI and Rucaparib Alone and in Combination A pentaerythritol-based multi-arm polymer conjugate of irinotecan ("PBMAPCI," obtained from Nektar Therapeutics, San Francisco Calif.), which is a long-acting topoisomerase I inhibitor, and rucaparib (Selleck Chemicals, Houston Tex.) were used in a combination study in an efficacy model of human breast cancer.

Cancerous cells from the BRCA1-deficient human breast cancer cell line, MX-1, were injected subcutaneously in female mice. Once tumors reached a size of approximately 100 mm$^3$ (63-196 mm$^3$), animals (n=10/group) were randomized into different treatment groups as follows: control; single agent rucaparib, 30 and 150 mg/kg; single agent PBMAPCI, 10 and 50 mg/kg; and four combination groups. Table 1 provides the treatment regimens in tabular form.

TABLE 1

Treatment Regimen

| | | Regimen 1 | | | | Regimen 2 | | |
|---|---|---|---|---|---|---|---|---|
| Gr. | N | Agent | Dose mg/kg | Route | Schedule | Agent | Dose mg/kg | Route | Schedule |
| 1[#] | 10 | vehicle | — | iv | qwk × 4 | — | — | — | — |
| 2 | 10 | rucaparib | 30 | po | q.d. × 21 | — | — | — | — |
| 3 | 10 | rucaparib | 150 | po | q.d. × 21 | — | — | — | — |
| 4 | 10 | PBMAPCI | 10 | iv | qwk × 4 | — | — | — | — |
| 5 | 10 | PBMAPCI | 50 | iv | qwk × 4 | — | — | — | — |
| 6 | 10 | rucaparib | 30 | po | q.d. × 21 | PBMAPCI | 10 | iv | qwk × 4 |
| 7 | 10 | rucaparib | 30 | po | q.d. × 21 | PBMAPCI | 50 | iv | qwk × 4 |
| 8 | 10 | rucaparib | 150 | po | q.d. × 21 | PBMAPCI | 10 | iv | qwk × 4 |
| 9 | 10 | rucaparib | 150 | po | q.d. × 21 | PBMAPCI | 50 | iv | qwk × 4 |

[#]Control group

Rucaparib was administered by oral gavage qd×21 and PBMAPCI was administered intravenously q7d×4, with treatment starting on Day 1. Animal weight, clinical observations and tumor volume were monitored twice/week until the endpoint (2000 mm$^3$ of tumor volume or Day 88) was met.

Efficacy was measured by tumor growth delay and regression response rate.

The results of the study are presented in FIG. 1 and Table 2. As is made evident in FIG. 1, despite the BRCA1 deficient status of the breast cancer cell line, single agent rucaparib was only marginally effective (at both the 30 mg/kg and 150 mg/kg dosages tested). PBMA PCI showed moderate efficacy at the 10 mg/kg level and complete regression at the 50/mg/kg level. The combination of both agents, however, showed synergy with the tumors of all ten animals regressing to a tumor-free status by 14-days after the start of treatment.

As is made evident in Table 2, PBMAPCI and rucaparib in combination showed marked synergy, demonstrated by durable complete responses even at the lowest doses of both agents. Moreover, it does not appear that dose reductions are required for either agent: the combination of PBMAPCI and rucaparib was well tolerated generally at all dose levels with no clinical signs and body weight loss, except for the combination of 150 mg/kg rucaparib and 50 mg/kg PBMAPCI, where individual animals showed body weight losses up to 15% (mean body weight loss for the group was only about 6%).

TABLE 2

Summary of Response

| Treatment Regimen | | Median TTE | T-C (days) | TGD (%) | Regressions (%) | | | Mean BW Nadir | Statistical Results For Groups Tested |
|---|---|---|---|---|---|---|---|---|---|
| Agent | mg/kg | | | | PR | CR | TFS | | |
| vehicle | — | 25 | — | — | 0 | 0 | 0 | — | |
| rucaparib | 30 | 39 | 14 | 56 | 0 | 0 | 0 | — | Significant against vehicle ($p \leq 0.05$) |
| rucaparib | 150 | 43 | 18 | 73 | 0 | 0 | 0 | — | Significant against vehicle ($p \leq 0.01$) |
| PBMAPCI | 10 | 57 | 32 | 129 | 0 | 10 | 10 | — | Significant against vehicle ($p \leq 0.001$) |
| PBMAPCI | 50 | 88 | 63 | 252 | 0 | 100 | 100 | — | Significant against vehicle ($p \leq 0.001$) |
| PBMAPCI + rucaparib | 10 + 30 | 88 | 63 | 252 | 0 | 100 | 100 | — | Significant against vehicle ($p \leq 0.001$), 10 mg/kg PBMAPCI ($p \leq 0.001$), 30 mg/kg rucaparib ($p \leq 0.001$) |
| PBMAPCI + rucaparib | 10 + 150 | 88 | 63 | 252 | 0 | 100 | 100 | — | Significant against vehicle ($p \leq 0.001$), 10 mg/kg PBMAPCI ($p \leq 0.001$), 150 mg/kg rucaparib ($p \leq 0.001$) |
| PBMAPCI + rucaparib | 50 + 30 | 88 | 63 | 252 | 0 | 100 | 100 | −0.6%, Day 3 | Significant against vehicle ($p \leq 0.001$), 30 mg/kg rucaparib ($p \leq 0.001$) |
| PBMAPCI + rucaparib | 50 + 150 | 88 | 63 | 252 | 0 | 100 | 100 | −6.4%, Day 5 | Significant against vehicle ($p \leq 0.001$), 150 mg/kg rucaparib ($p \leq 0.001$) |

Example 2

Efficacy of Treatment Using PBMAPCI and BMN 673 in Combination in a Human Lung Small Cell Carcinoma Model A pentaerythritol-based multi-arm polymer conjugate of irinotecan ("PBMAPCI," obtained from Nektar Therapeutics, San Francisco Calif.), which is a long-acting topoisomerase I inhibitor, and BMN 673 (BioMarin, San Rafael Calif.) were used in a combination study in an efficacy model of human breast cancer.

Cancerous cells from the NCI-H1048 human lung small cell carcinoma line were injected into BALB/c nude mice. Once tumors reached a size of approximately 100 mm³-200 mm³, animals (n=10/group) were randomized into different treatment groups as identified in Table 3 and administered test article(s) as indicated. Mice were to have body weights of greater than 20 g at time of test article dosing and were checked daily, with tumor size and body weights checked twice a week through the test period. A "drug holiday," in which no test articles were administered, was undertaken for any animal that exhibited a body weight loss of greater than 20%.

TABLE 3

Treatment Regimen

| Group | n | Treatment | Dose (mg/kg) | Dosing volume | Dosing route | Schedule |
|---|---|---|---|---|---|---|
| 1 | 10 | Vehicle 1 | — | 10 ul/g | Oral | Daily × 14 days |
|   |    | Vehicle 2 |   | 10 ul/g | Intravenous | Day 2 |
| 2 | 10 | Vehicle 1 | — | 10 ul/g | Oral | Daily × 14 days |
|   |    | PBMAPCI | 543 | 10 ul/g | Intravenous | Day 2 |
| 3 | 10 | Vehicle 1 | — | 10 ul/g | Oral | Daily × 14 days |
|   |    | PBMAPCI | 102 | 10 ul/g | Intravenous | Day 2 |
| 4 | 10 | BMN 673 | 0.2 | 10 ul/g | Oral | Daily × 14 days |
|   |    | Vehicle 2 | — | 10 ul/g | Oral | Day 2 |
| 5 | 10 | BMN 673 | 0.3 | 10 ul/g | Oral | Daily × 14 days |
|   |    | Vehicle 2 | — | 10 ul/g | Intravenous | Day 2 |
| 6 | 10 | BMN 673 | 0.2 | 10 ul/g | Oral | Daily × 14 days |
|   |    | PBMAPCI | 543 | 10 ul/g | Intravenous | Day 2 |
| 7 | 10 | BMN 673 | 0.2 | 10 ul/g | Oral | Daily × 14 days |
|   |    | PBMAPCI | 109 | 10 ul/g | Intravenous | Day 2 |
| 8 | 10 | BMN 673 | 0.3 | 10 ul/g | Oral | Daily × 14 days |
|   |    | PBMAPCI | 109 | 10 ul/g | Intravenous | Day 2 |

Figure 2:
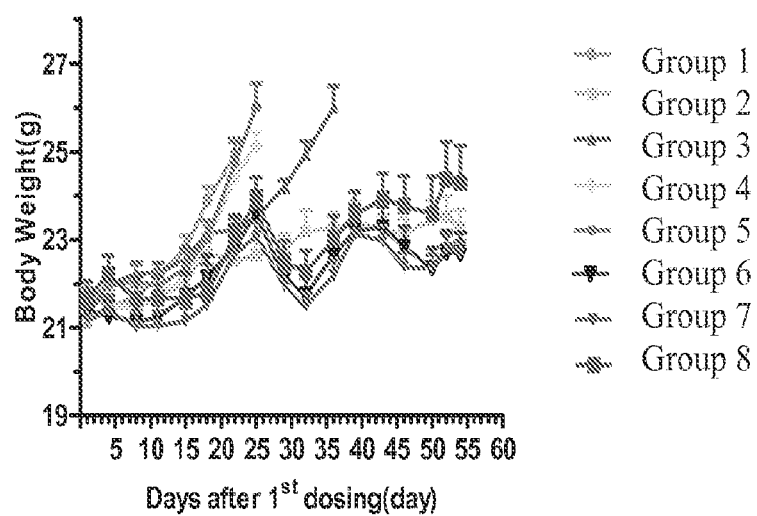
FIG. 2 shows the mean body weights of mice in various treatment groups in a H1048 lung small cell carcinoma model conducted as described in Example 2.
Figure 3:
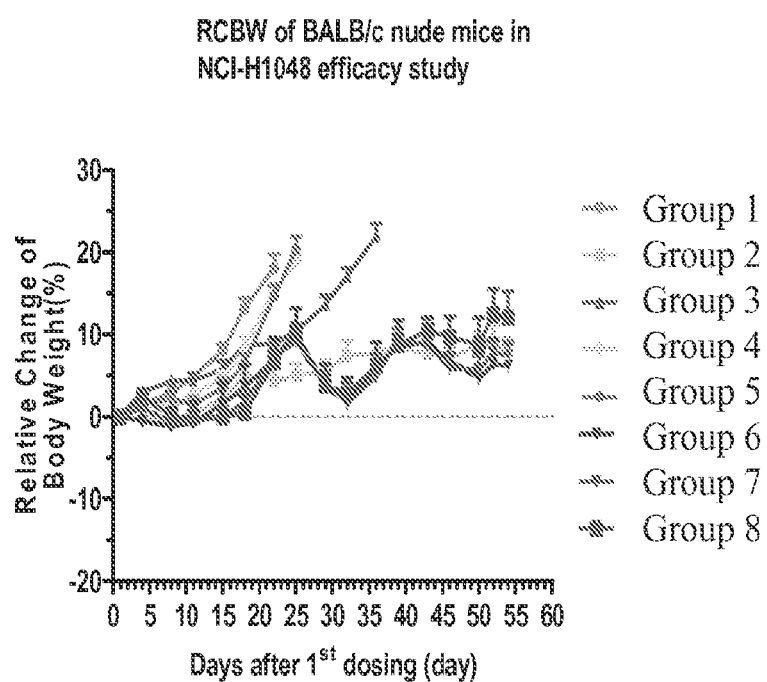
FIG. 3 shows the relative change of body weights of mice in various treatment groups in a H1048 lung small cell carcinoma model conducted as described in Example 2.
Figure 4:
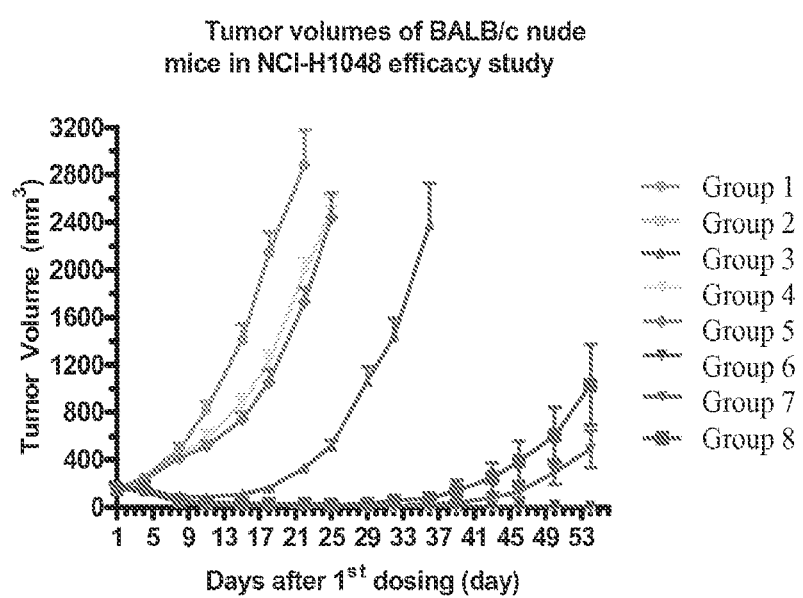
FIG. 4 shows mean tumor volumes in various treatment groups of a H1048 lung small cell carcinoma model in mice conducted as described in Example 2.

The average body weights, relative change in body weights and tumor volumes for each of the eight different treatment groups measured over the course of the study are provided in FIG. 2, FIG. 3 and FIG. 4, respectively.

What is claimed is:

1. A method of treating a patient having BRCA1-deficient breast cancer, the method comprising the steps of: (a) administering to the patient having BRCA1-deficient breast cancer, a PARP-inhibiting amount of rucaparib; and (b) administering to the patient a topoisomerase I-inhibiting amount of a long-acting topoisomerase I inhibitor having a structure:

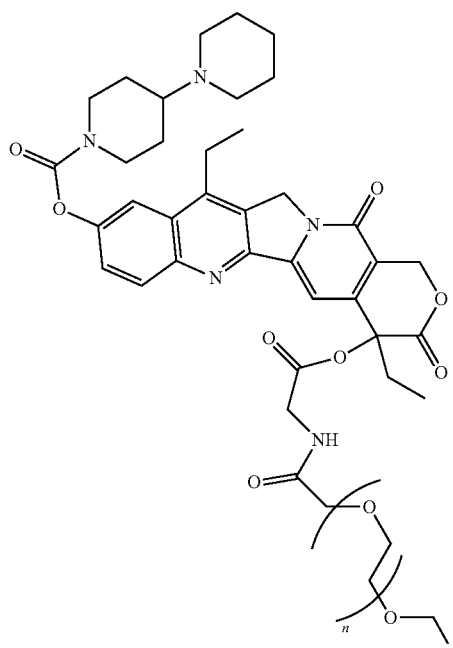
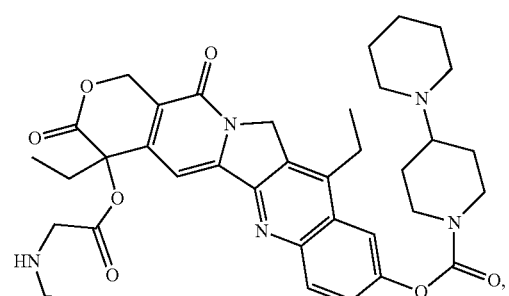

-continued

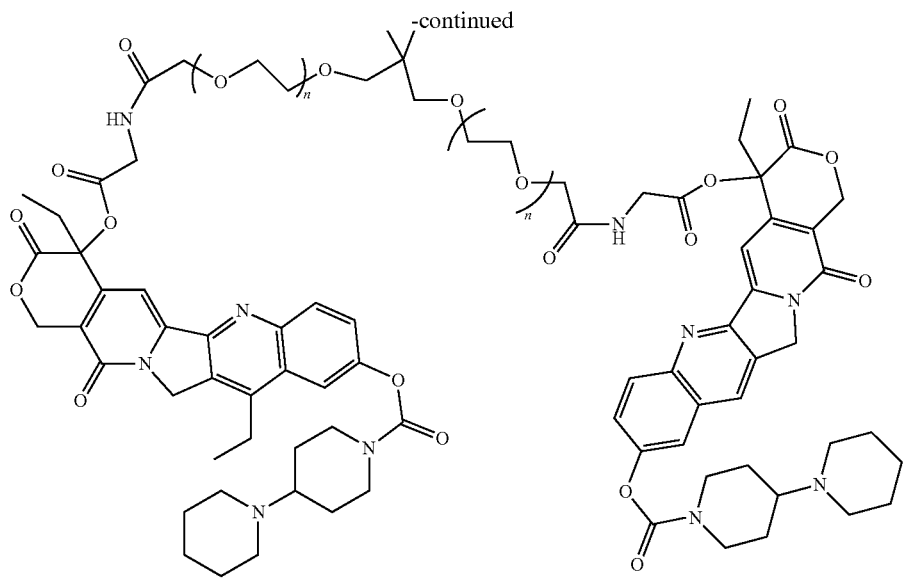

where each n is about 113;
or pharmaceutically acceptable salts thereof.

2. The method of claim 1, wherein the patient is human.

3. The method of claim 1, wherein step (a) is carried out prior to step (b) being carried out.

4. The method of claim 1, wherein (a) is carried out after step (b) is carried out.

5. The method of claim 1, wherein steps (a) and (b) are carried out simultaneously.

6. The method of claim 1, wherein each of steps (a) and (b) are carried out at least twice, followed by a maintenance phase wherein the patient is administered a PARP-inhibiting amount of rucaparib without any further administration of the long-acting topoisomerase I inhibitor.

7. The method of claim 1, wherein rucaparib is administered orally.

8. The method of claim 1, wherein the long-acting topoisomerase I inhibitor, or a pharmaceutically acceptable salt form thereof, is administered parenterally.

9. The method of claim 8, wherein the long-acting topoisomerase I inhibitor, or a pharmaceutically acceptable salt form thereof, is administered intravenously.

10. The method of claim 1, wherein the combination of rucaparib and the long-acting topoisomerase I inhibitor, when evaluated in a mouse model for BRCA1-deficient breast cancer, demonstrates a synergistic effect.

11. The method of claim 2, wherein the topoisomerase I-inhibiting amount of the long-acting topoisomerase I inhibitor is in a range of from about 30 mg/m$^2$ to about 200 mg/m$^2$.

* * * * *